United States Patent [19]

Wang et al.

[11] Patent Number: 4,921,582
[45] Date of Patent: May 1, 1990

[54] DISSOLVED OXYGEN MEASURING METHOD

[76] Inventors: Henry Y. Wang, 2488 Bunker Hill Rd., Ann Arbor, Mich. 48105; Xiang M. Li, Research Inst. of Chem. Eng., SCIT, Guangzhou, China

[21] Appl. No.: 93,340

[22] Filed: Sep. 4, 1987

[51] Int. Cl.$^5$ ............................................. G01N 27/46
[52] U.S. Cl. ................................ 204/153.1; 204/400; 204/415
[58] Field of Search ............... 204/1 P, 415, 402, 400

[56] References Cited

U.S. PATENT DOCUMENTS

| | | | |
|---|---|---|---|
| 3,098,813 | 7/1963 | Beebe et al. | 204/415 |
| 3,454,485 | 7/1969 | Hauk et al. | 204/415 |
| 3,493,485 | 2/1970 | MacArthur | 204/415 |
| 3,509,034 | 4/1970 | Paine | 204/415 |
| 4,272,330 | 6/1981 | Hetrick | 204/1 T |
| 4,464,230 | 8/1984 | Langdon | 204/1 T |
| 4,543,176 | 9/1985 | Harada et al. | 204/406 |
| 4,556,472 | 12/1985 | Langdon | 204/406 |
| 4,595,485 | 6/1986 | Takahashi et al. | 204/406 |
| 4,601,809 | 7/1986 | Kitahara | 204/406 |
| 4,622,125 | 11/1986 | Oyama et al. | 204/406 |
| 4,735,691 | 4/1988 | Green et al. | 204/415 |

OTHER PUBLICATIONS

Langdon, "Dissolved Oxygen Monitoring System Using a Pulsed Electrode: Design, Performance, and Evaluation", *Deep-Sea Research*, vol. 31, No. 11, pp. 1357–1367, 1984.

*Primary Examiner*—T. Tung
*Attorney, Agent, or Firm*—Rohm & Monsanto

[57] ABSTRACT

A system for measuring dissolved oxygen in a fluid employs a galvanic electrode operated in a transient mode. In operation, the galvanic electrode is intermittently coupled and decoupled, under computer control, to and from a sampling system. The sampling system samples the transient current which results from the intermittency, and generates a current-time curve. Prior to the first use of the galvanic electrode, however, the galvanic electrode is calibrated, a theoretical current-time curve is generated, and the residual current of the galvanic electrode is recorded. Such calibration and residual current data is used to generate simulation data corresponding to a simulation curve. The concentration of dissolved oxygen in the test fluid is determined using the simulation data.

12 Claims, 3 Drawing Sheets

DISSOLVED OXYGEN MEASURING METHOD

BACKGROUND OF THE INVENTION

This invention relates generally to systems for measuring and monitoring dissolved oxygen, and more particularly, to a novel galvanic electrode system which is operated under computer control in a transient mode by programmed on-off cycling.

The need to measure and monitor concentrations of dissolved oxygen is present in a large variety of processes, including biological processes such as aerobic fermentation and waste treatment plants. However, currently available systems for measuring dissolved oxygen suffer from a variety of significant disadvantages. For example, one system in common use employs a polarographic electrode, which operates under Fick's law of diffusion through a membrane. This type of electrode requires a very stable power supply for supplying the polarizing voltage. In addition to increasing the complexity, down-time, and expense of the system, such a power supply also increases its bulk.

In operation, the polarographic electrode is energized by the application of a voltage, and the oxygen within an electrolyte in the electrode is consumed. A measured electrical current between the cathode and anode is responsive to the rate of diffusion of oxygen through the membrane of the polarographic electrode, to the surface of a cathode. It is evident that systems which use polarographic electrodes to measure dissolved oxygen are slow in reacting since it is known that diffusion through the membrane is a slow process. The slowness of operation of polarographic electrode devices is particularly disadvantageous in the monitoring of streams of fluid. In addition, such systems are not only prone to drift in calibration over time, they are also sensitive to motion of the specimen fluid, such as may result from stirring when operated in the steady state mode.

The prior art has thrust at some of these problems by employing polarographic electrode systems in pulsed mode of operation. Control over the measurement process is achieved by computer, including the duration of periods of energization and the periods therebetween. However, the algorithm used in known systems for computation of the dissolved oxygen concentration from the response of the polarographic electrode applies a linear relation constraint, which results in a long delay time, typically on the order of 1.5-3 seconds, and a long recovery time, typically greater than 3 minutes. During the delay and recovery periods, the known system is incapable of detecting dissolved oxygen. In fact, the prior art acknowledges that approximately 1.5 seconds is the shortest usable delay time if nonlinearity is to be avoided.

In addition to the foregoing, known pulsed polarographic electrode systems are incapable of reading calibration data on-line. This, when coupled with the fact that multiple programs must be run to perform the various functions of acquiring data, controlling hardware, and generating data, render the known systems difficult to operate.

A galvanic electrode is easier to use than a polarographic electrode, since it does not require application of an external voltage. Instead, the galvanic electrode generates an internal potential responsive to the oxygen flux reaching the cathode. To date, however, galvanic electrodes have been used only in a steady state mode.

The steady state current depends on two primary factors, the first of which is the oxygen tension in the test solution. The steady state current is directly proportional to the oxygen concentration in the bulk solution, which dictates the driving force of the of the oxygen transport.

The second factor is the total mass transfer resistance between the test solution and the cathode. This resistance includes the resistance within the electrode, such as the electrolyte layer and the membrane, and the resistance outside of the electrode, which includes fouling and boundary layer effects. Particularly in many fermentation processes, fouling can occur at the membrane surface, resulting in an increase of the mass transfer resistance. Such fouling results in the introduction of significant error in the measurement because, in steady state operation, the outside resistances change with time and therefore have an uncalibrated effect on the oxygen flux. One known approach to reduce these effects involves the use of thicker membranes. The greater thickness of the membrane, however, disadvantageously reduces the sensitivity of the electrode, and increases the response time.

It is, therefore, an object of this invention to provide a simple and economical system for measuring accurately a concentration of dissolved oxygen.

It is another object of this invention to provide a dissolved oxygen measurement system which is readily controllable by computer.

It is also an object of this invention to provide a dissolved oxygen measurement arrangement can operate without an external voltage source.

It is a further object of this invention to provide a dissolved oxygen measurement system which can be calibrated under computer control.

It is additionally an object of this invention to provide a dissolved oxygen measurement arrangement which does not require platinum or gold in its cathode.

It is yet a further object of this invention to provide a dissolved oxygen measurement arrangement which is not sensitive to membrane fouling.

It is also another object of this invention to provide a dissolved oxygen measurement arrangement which is not sensitive to variations in speed of motion of the tested fluid.

It is yet an additional object of this invention to provide a dissolved oxygen measurement arrangement which is not sensitive to viscosity of the fluid being tested.

It is still another object of this invention to provide a dissolved oxygen measurement system which is more reliable than the presently known systems, and which is subject to less downtime.

It is a yet further object of this invention to provide a dissolved oxygen measurement system in which an algorithm is used to compute dissolved oxygen concentration.

It is also a further object of this invention to provide a system which determines a concentration of dissolved oxygen using an algorithm which is not subject to a linear relation constraint.

It is additionally another object of this invention to provide a dissolved oxygen measurement system having a low sampling delay characteristic.

A still further object of this invention is to provide a dissolved oxygen measurement arrangement having a short recovery time.

An additional object of this invention is to provide a dissolved oxygen measuring system which is capable of reading calibration data on-line.

Another object of this invention is to provide a galvanic electrode for measuring dissolved oxygen in a fluid and which is not sensitive to back diffusion of oxygen from the electrolyte.

SUMMARY OF THE INVENTION

The foregoing and other objects are achieved by this invention which provides, in accordance with a method aspect thereof, a method of measuring dissolved oxygen in a test fluid having a concentration of dissolved oxygen desired to be measured. In accordance with the invention, the method includes the steps of inserting a galvanic electrode into the test fluid, and coupling intermittently the galvanic electrode via a coupling circuit to an electrical monitoring system, whereby an intermittent electric current having a transient characteristic is caused to flow in the coupling circuit. A sample signal is produced corresponding to a sample of at least a transient characteristic of the intermittent electric current in the coupling circuit.

The intermittent coupling is effected, in a specific illustrative embodiment of the invention, by operating a switching device under control of a computer. Also, an amplification device can be used to produce an amplified signal corresponding to the intermittent electric current, prior to sampling.

Prior to performing a measurement of dissolved oxygen in a test fluid, there is provided the further step of residual-sampling in a transient mode of operation a residual signal responsive to a residual current in the galvanic electrode. The residual-sampling is performed at a plurality of temperature levels, and for each such performance of residual-sampling there is provided the further step of residual-storing residual current data responsive to respectively associated performances of the residual-sampling.

Also prior to performing a measurement of dissolved oxygen in a test fluid, the galvanic electrode is calibrated by placing same in a calibration solution having a known oxygen concentration, and calibration-sampling, in a transient mode of operation, a calibration signal responsive to a calibration current in the galvanic electrode. The resulting calibration data obtained during the calibration-sampling corresponds to a transient calibration current-time curve, which is stored in memory.

From the stored calibration data is computed a plurality of system parameters. Such parameters may include a surface parameter value corresponding to active surface of a cathode of the galvanic electrode; a thickness parameter value corresponding to a thickness of a layer of an electrolyte of the galvanic electrode; and a diffusivity parameter value corresponding to a diffusivity of oxygen in the electrolyte. Using these parameter values, a theoretical current-time curve for the galvanic electrode is computed.

A simulated current-time curve is computed by superimposing the residual current data on the theoretical current-time curve, to produce simulation data. A parameter estimation computing routine is applied to determine a plurality of best-fit parameters corresponding to minimization of least square errors between the simulation data corresponding to the simulated current-time curve and the calibration data corresponding to the transient calibration current-time curve. The best-fit parameter values are stored for use later during measurement of dissolved oxygen in the test fluid. Preferably, the calibration procedure is performed in at least three temperature levels. At each such temperature level, one to ten concentration settings can be used for calibration.

In accordance with an apparatus aspect of the invention, a galvanic electrode arrangement is disclosed for measuring characteristic components in fluids. The galvanic electrode is of the type having a body adapted for containing an electrolyte, illustratively 1M $K_2HPO_4$, and is provided with a cathode formed of a spiral silver wire. In accordance with the invention, a membrane is arranged to close one end of the body of the galvanic electrode arrangement. The membrane may be formed, in certain embodiments, of 1 mil thick Teflon, such as is marketed by DuPont FEP, Wilmington, Del. However, the membrane may have a thickness of approximately between 0.01 mm to 0.05 mm. An anode, which may be formed of lead, is disposed within the body of the galvanic electrode arrangement and in communication with the electrolyte.

In a specific embodiment of the invention, the cathode of the galvanic electrode arrangement is a silver wire which is adhered on its back side to a plastic sheet insulation on one side of an insulator formed of a metal sheet having a layer of plastic sheet insulation arranged on each side thereof. This insulator on the back side of the cathode serves to minimize the back diffusion of oxygen from the electrolyte. The front side of the silver wire cathode is roughened, illustratively by the application of sandpaper, to ensure that a layer of the electrolyte is accommodated between the cathode and the membrane. In other embodiments, the back side of the cathode may be insulated with an insulating coating, such as epoxy.

As noted hereinabove, the system of the present invention is further provided with a sampling arrangement for sampling a transient signal. A coupling circuit having a switching member associated therewith is used to couple and decouple intermittently a selectable one of the cathode and the anode to and from the sampling arrangement. In this manner, a transient signal is produced in the coupling circuit. A control system, which may be a computer system in certain embodiments, controls the operation of the sampling arrangement and the switching member.

A four-layer model was developed by the inventors herein to describe the behaviors of the electrode. The four layers are: (1) electrolyte, (2) membrane, (3) fouling, and (4) boundary layer. The oxygen transport processes in these four layers are described by the following equations:

$$\frac{\partial a_i}{\partial t} = D_i \frac{\partial^2 a_i}{\partial x^2}, \text{ for } i = 1, 2, 3, 4 \quad \text{Eq. 1}$$

Eq. 1 is the Fick's second law applied to these four different layers. The oxygen activity $a(=\tau C)$ is considered as the transport driving force.

$$\frac{a_i}{S_i} = \frac{a_{i+1}}{S_{i+1}}, \text{ at } x_i, i = 1, 2, 3 \quad \text{Eq. 2}$$

$$D_i \frac{\partial a_i}{\partial x} = D_{i+1} \frac{\partial a_{i+1}}{\partial x}, \text{ at } x_i, i = 1, 2, 3 \quad \text{Eq. 3}$$

-continued $$a_4 = \tau_4 C_s, \text{ at } x_4 \quad \text{Eq. 4}$$

Eq. 2 and Eq. 3 are equilibrium and mass conservation conditions at the boundaries between adjacent layers. In Eq. 4, the oxygen activity at the outer surface of the boundary layer is assumed equal to the product of the activity coefficient and the bulk concentration.

$$\text{during time on: } a_1 = \tau_1 C_1 = 0, \text{ at } x = 0 \quad \text{Eq. 5}$$

$$\text{during time off: } \frac{\partial a_i}{\partial x} = 0 \quad \text{Eq. 6}$$

Eq. 5 is the boundary condition at the cathode surface during time on. Since the reduction of oxygen at the cathode is much faster than oxygen transport, the oxygen concentration at the cathode surface is assumed to be zero. Eq. 6 is the impermeable condition at the cathode during time off. In this time period, the oxygen reduction stops, and oxygen concentration in the electrolyte layer and the membrane is replenished.

at $t = 0$, $$a_4 = \tau_4 C_s; \quad \text{Eq. 7}$$

$$a_3 = a_4/S_4 \times S_3; \quad \text{Eq. 8}$$

$$a_2 = a_3/S_3 \times S_2; \text{ and} \quad \text{Eq. 9}$$

$$a_1 = a_2/S_2 \times S_1. \quad \text{Eq. 10}$$

In Eqs. 7-10, the initial oxygen concentrations in these four layers are assumed to be in equilibrium.

Current output equation:

$$i = FAN\tau_1 D_1 \frac{\partial C_1}{\partial x}, \text{ at } x = 0 \quad \text{Eq. 11}$$

Where:
A—active surface area of cathode, cm$^2$
a—activity of oxygen
C—oxygen concentration, gmol/cm$^3$
D—diffusivity of oxygen, cm/sec
F—Faraday constant, $9.65 \times 10^4$ col/gmol
i—current output, A
L—thickness, cm
$S_i$—solubility of oxygen in i$^{th}$ layer, gmol/cm$^3$/cmHg
t—time, sec
x—space coordinate, cm
$\tau$—activity coefficient of oxygen
Subscript i—for i$^{th}$ layer
Subscript s—bulk solution

BRIEF DESCRIPTION OF THE DRAWING

Comprehension of the invention is facilitated by reading the following detailed description, in conjunction with the annexed drawing, in which.

DETAILED DESCRIPTION

Figure 1:
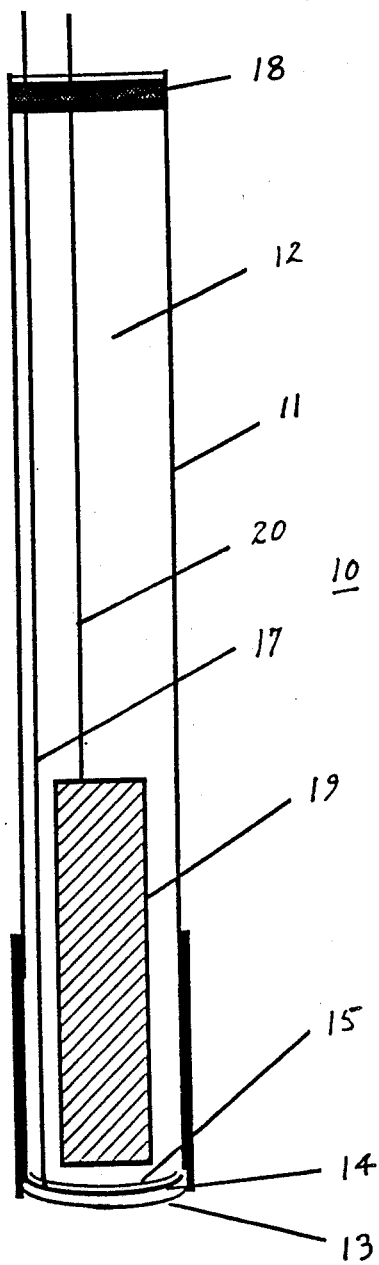
FIG. 1 is a schematic representation of a galvanic electrode constructed in accordance with the principles of the invention.

FIG. 1 is a schematic representation of a galvanic electrode 10 constructed in accordance with the principles of the invention. The galvanic electrode is contained generally within a glass tube 11 which has disposed therewithin an electrolyte 12. The electrolyte used in this embodiment may be 1M K$_2$HPO$_4$. A membrane 13, which may be formed of Teflon, closes the lowermost portion of glass tube 11, preventing escape of electrolyte 12. The membrane, however, permits passage therethrough of oxygen, at a rate which is governed in large measure by the parameters thereof. Thus, for example, a thicker membrane presents a greater impedance to the passage of the oxygen.

A cathode 14 is disposed within glass tube 11 in the vicinity of membrane 13. In a practical embodiment of the invention, the cathode is formed of silver wire, preferably of a spiral type. Immediately above cathode 14 is an insulator 15 which may be formed of a sheet of metal coated on both sides with plastic sheet (not shown). Insulator 15 preferably is adhered to cathode 14, and serves to minimize the back diffusion of oxygen from electrolyte 12. Thus, the sensing action of galvanic electrode 10 is essentially localized to the vicinity of membrane 13, thereby decreasing delay and recovery times. Cathode 14 is coupled electrically to a lead 17 which extends through a seal 18, outside of galvanic electrode 10.

Galvanic electrode 10 is further with an anode 19 which is arranged within glass tube 11 and in communication with electrolyte 12. The anode is electrically coupled to a lead 20 which also extends out of glass tube 11 through seal 18. In a practical embodiment, the anode is formed of lead.

Figure 2:
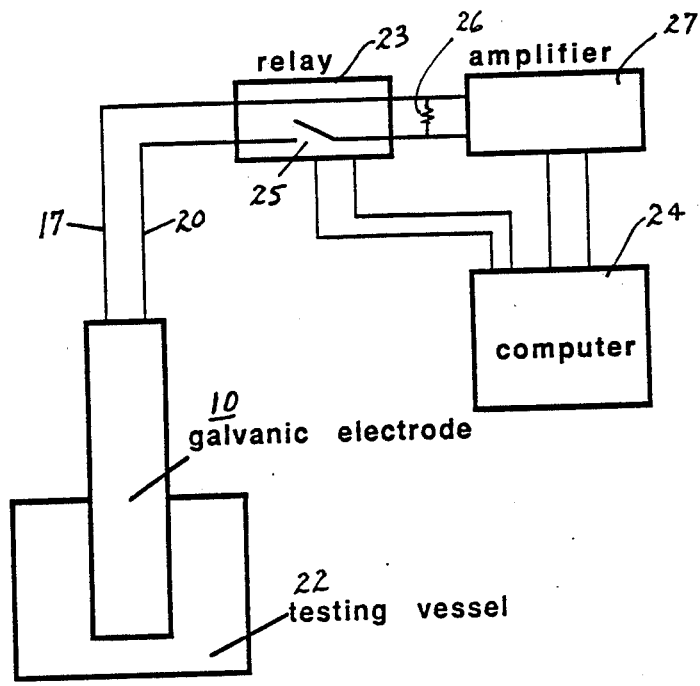
FIG. 2 is a simplified block and line representation of a system for measuring dissolved oxygen using the galvanic electrode of FIG. 1.

FIG. 2 is a simplified block and line representation of a system for measuring dissolved oxygen using galvanic electrode 10 of FIG. 1. As shown, the galvanic electrode is immersed in a test fluid (not shown) within a testing vessel 22. In certain embodiments, testing vessel 22 may have associated therewith one or more of a variety of accessories which are known to be usable with such vessels, such as a temperature controller (not shown), a stirrer (not shown), and one or more supplies (not shown) of gasses to be dissolved in the test fluid.

Galvanic electrode 10 is coupled electrically via its leads 17 and 20 to a relay 23. This relay is controlled by a computer 24, and by means of switching contacts 25, galvanic electrode 10 is intermittently coupled and decoupled from a coupling circuit which includes a resistor 26. Such intermittent operation of switching contacts 25 causes a current flowing through resistor 26 to be interrupted, thereby causing transient effects. In this specific embodiment, the resulting transient voltage across resistor 26 is sensed by an amplifier 27 which is coupled at its input to resistor 26. Of course, in certain embodiments, amplifier 27 may not be necessary, and in still other embodiments, resistor 26 may not be necessary since the transient effects may be sensed across an input impedance of the amplifier.

The transient portion of the signal at the output of amplifier 27, which corresponds to the current through resistor 26, is conducted to computer 24, where it is sampled to produce a current-time curve. The data corresponding to the current-time curve is compared to calibration data stored in the computer, and in certain embodiments, with data corresponding to residual current within galvanic electrode 10, to produce an estimate of the actual concentration of oxygen in the test fluid.

Figure 3:
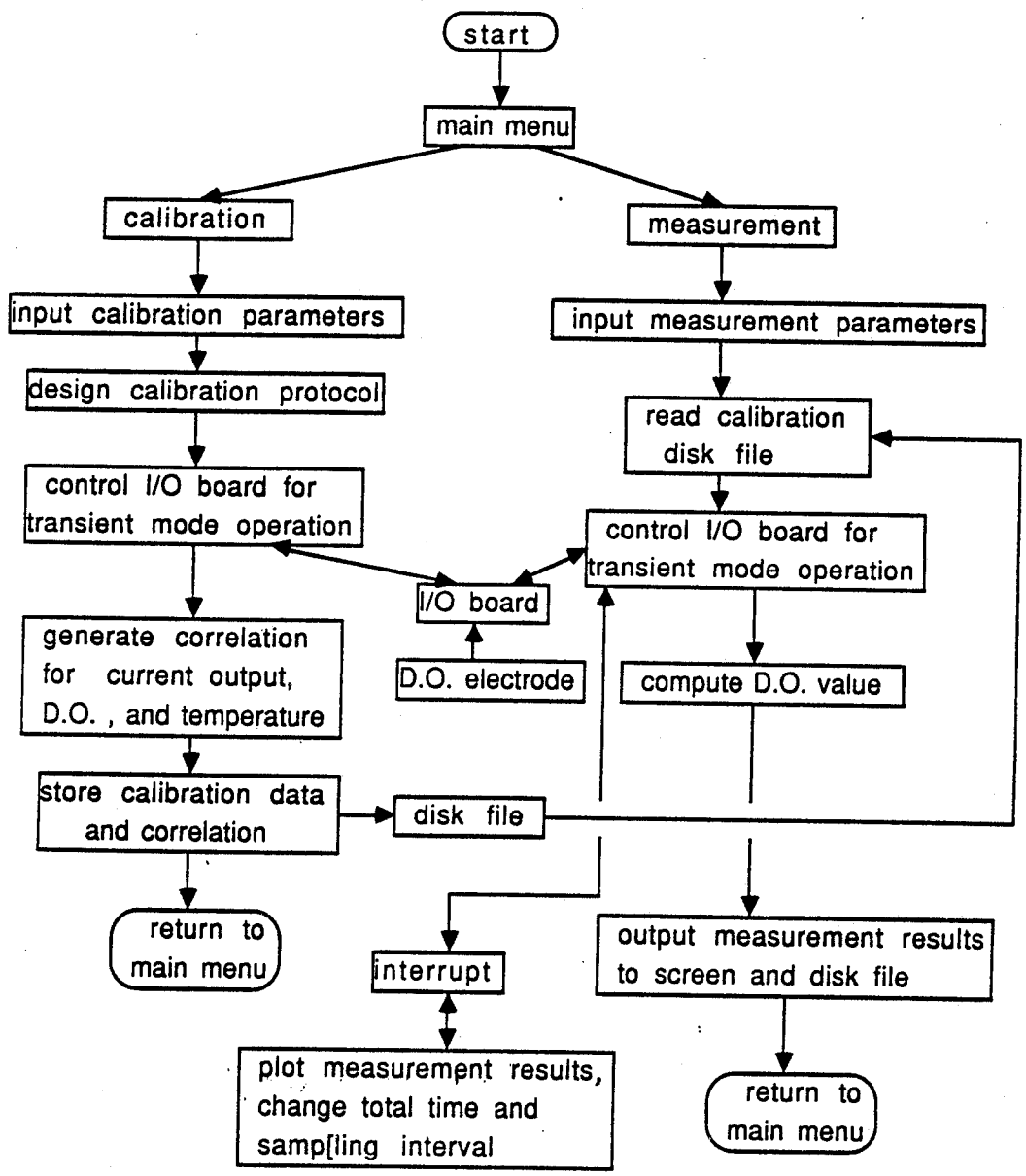
FIG. 3 is a function block representation of a process for operating the system of FIG. 2.

FIG. 3 is a function block representation of a process for operating the system of FIG. 2, using the computer. As shown, the inventive process has essentially two branches, one for calibration and one for measurement. The system begins by bringing up a main menu which permits the user to select between measurement and calibration functions.

When calibration is selected, the galvanic electrode is placed in a solution with known oxygen concentration. The current-time curve is sampled in a transient mode, by control of an I/O board by the computer. The system parameters, such as the active surface of the cathode, thickness of the electrolyte layer, and the diffusivity of oxygen in the electrolyte will be estimated by using a parameters estimation technique with the measured current-time curve. With an initial set of parameters, computer simulation, which is based on solving numerically a plurality of equations (Eq. 1-Eq. 11, above) using a Finite Difference Method, will generate a theoretical current-time curve. The simulated current-time curve is obtained by superimposing the residual current to the theoretical current-time curve. The parameter estimation routine is used to search the best parameters which can minimize the least square errors between the simulated results and the measured current-time curve. The best-fit parameters will be stored in data files for further application in measurement. The calibration is performed at three temperature levels. At each temperature level, one to ten concentration settings can be used for calibration.

During measurement of dissolved oxygen, the unknown parameter files obtained during calibration are retrieved and used for estimating oxygen concentration based on the measured current-time curve. Once again, the I/O board is controlled to effect the transient mode of operation. If the temperature in the solution is not the same as the temperature in calibration, the system parameters will be interpolated using second order Lagrange polynomial according to the temperature.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of measuring dissolved oxygen in a test fluid having a concentration of dissolved oxygen desired to be measured, the method comprising the steps of:
   residual sampling in a transient mode of operation a residual signal responsive to a residual current in a galvanic electrode arrangement for obtaining characteristic data corresponding to a characteristic of said galvanic electrode arrangement;
   calibrating said galvanic electrode arrangement with respect to said characteristic data;
   inserting said galvanic electrode arrangement into the test fluid, said galvanic electrode arrangement having anode and cathode electrodes for producing an output potential therebetween responsive to an oxygen flux which communicates with said cathode electrode via an oxygen-permeable membrane interposed between said cathode electrode and the test fluid;
   coupling intermittently said galvanic electrode arrangement via a coupling circuit to an electrical monitoring system, whereby an intermittent electric current which is generated in said galvanic electrode arrangement is caused to flow in said coupling circuit; and
   producing a sample signal corresponding to a sample of at least a transient characteristic of said intermittent electric current in said coupling circuit.

2. The method of claim 1 wherein said step of coupling intermittently comprises the step of operating a switching device under computer control.

3. The method of claim 1 wherein said step of producing a sample signal comprises the step of amplifying a signal corresponding to said intermittent electric current.

4. The method of claim 1 wherein said step of residual sampling is performed at a plurality of temperature levels, and for each such performance of said step of residual sampling there is provided the further step of residual storing residual current data responsive to respectively associated performances of said step of residual sampling.

5. The method of claim 1 wherein said step of calibrating comprises the steps of:
   placing said galvanic electrode arrangement in a calibration solution having a known oxygen concentration;
   calibration sampling in a transient mode of operation a calibration signal responsive to a calibration current in said galvanic electrode arrangement; and
   calibration storing calibration data obtained during said step of calibration sampling, said calibration data corresponding to a transient calibration current-time curve.

6. The method of claim 5 wherein said step of calibrating comprises the further step calibration computing from said stored calibration data a plurality of system parameters.

7. The method of claim 6 wherein said step of calibration computing comprises the steps of:
   surface computing a surface parameter value corresponding to an active surface of the cathode of said galvanic electrode arrangement;
   thickness computing a thickness parameter value corresponding to a thickness of a layer of an electrolyte of said galvanic electrode arrangement;
   diffusivity computing a diffusivity parameter value corresponding to a diffusivity of oxygen in said electrolyte; and
   theoretical curve computing a theoretical current-time curve for said galvanic electrode arrangement.

8. The method of claim 7 wherein there is provided the further step of simulated curve computing comprising the step of superimposing said residual current data on said theoretical current-time curve, to produce simulation data corresponding to a simulated current-time curve.

9. The method of claim 8 wherein there are provided the further steps of:
   best-fit computing a plurality of best-fit parameters corresponding to minimization of least square errors between said simulation data corresponding to said simulated current-time curve and said calibration data corresponding to said transient calibration current-time curve; and parameter storing a plurality of best-fit parameter values corresponding to said best-fit parameters.

10. The method of claim 9 wherein said step of parameter storing is performed for a plurality of best-fit parameter values corresponding to a plurality of calibration temperatures.

11. The method of claim 9 wherein there is further provided the step of interpolating using ones of said best-fit parameter values corresponding to different calibration temperatures in response to a test temperature of said test fluid, when said test temperature is different from said calibration temperatures.

12. A method of measuring the concentration of dissolved oxygen in a test fluid, the method comprising the steps of:

producing calibration data for a galvanic electrode arrangement at a plurality of temperatures and for a plurality of concentrations of dissolved oxygen;

determining a residual current value for said galvanic electrode arrangement;

combining said calibration data and said residual current value to produce simulation data corresponding to a simulated current-time curve and a plurality of system parameters;

sampling a transient characteristic of a current which is generated by said galvanic electrode arrangement in the test fluid and which flows through a coupling circuit and a load, said galvanic electrode arrangement having anode and cathode electrodes for producing an output potential therebetween responsive to an oxygen flux which communicates with said cathode electrode via an oxygen-permeable membrane interposed between said cathode electrode and the test fluid, said transient characteristic being produced by intermittently changing the magnitude of said current flowing in said coupling circuit;

producing characteristic data responsive to said step of sampling, said characteristic data corresponding to a current-time curve; and comparing said characteristic data to said simulation data of said galvanic electrode arrangement to produce difference data, said difference data corresponding to the concentration of dissolved oxygen in the test fluid.

* * * * *